United States Patent
Shah et al.

(10) Patent No.: US 6,818,636 B2
(45) Date of Patent: Nov. 16, 2004

(54) B-RING ESTRATRIENES

(75) Inventors: Syed M. Shah, East Hanover, NJ (US); Panolil Raveendranath, Monroe, NY (US); Michael Z. Kagan, Plainsboro, NJ (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 10/348,506

(22) Filed: Jan. 21, 2003

(65) Prior Publication Data

US 2003/0109513 A1 Jun. 12, 2003

Related U.S. Application Data

(62) Division of application No. 09/063,524, filed on Apr. 21, 1998, now Pat. No. 6,525,039.
(60) Provisional application No. 60/045,422, filed on May 2, 1997.

(51) Int. Cl.$^7$ ............................................. A61K 31/56
(52) U.S. Cl. ........................ 514/179; 514/178; 514/824
(58) Field of Search ................................. 514/178, 179

(56) References Cited

U.S. PATENT DOCUMENTS

| | | |
|---|---|---|
| 2,834,712 A | 5/1958 | Beall et al. |
| 3,608,077 A | 9/1971 | Ginsig |
| 4,154,820 A | 5/1979 | Simons |
| 5,545,635 A | 8/1996 | Bryant et al. |

FOREIGN PATENT DOCUMENTS

| | | |
|---|---|---|
| DE | 635781 | 10/1936 |
| GB | 864231 | 3/1961 |

OTHER PUBLICATIONS

Physician Desk Reference, 48$^{th}$ Edition, pp. 2594–2596, 1994.*
Goodman and Gilman, Seventh Edition, pp. 1420–1429, 1985.*
Banerjee, D.K., et al., Indian J. Chem, 1969, 7 pp. 529–532.
Chem Abstract, CA64:11509a.
Chem Abstract, CA65:2576b.
Chem Abstract, CA54:9030h.
Johnson, R. et al., J. Pharma. Sci., 67(9), Sep. 1978, pp. 1218–1224.
Junghans, K., et al., Chem. Ber., 112(7), 1979, pp. 2631–2639.
Chemical Abstracts, 106(25), Jun. 22, 1987, No. 207882.
Chemical Abstracts, 6(21), May 22, 1967, No. 92028.
Kocovsky, P., et al., Coll. of Czechos. Chem. Communic., 39(7), 1974, pp. 1905–1913.
Bachmann, W.E. et al., Helv. Chim. Acta., 42(6), Oct. 15, 1959, pp. 1790–1793.
Eimasry, A.H., et al., J. Pharm. Sci., 59(4), Apr. 1970, pp. 449–458.
Schuller, W.H., et al., J. Med. Chem., 14(5), May 1971, p. 466.
Peters, R.H., et al., J. Med. Chem. 32(7), Jul. 1989, pp. 1642–1652.
Physicians Desk Reference, 48$^{th}$ edition, pp. 2594–2596, 1994.
Goodman and Gilman, seventh edition, pp. 1420–1429, 1985.
Starka et al., Chem. Abstract, CA64:11509a, 1966.
Starka et al., Chem. Abstract, CA65:2576b, 1966.

* cited by examiner

*Primary Examiner*—Barbara P. Badio
(74) *Attorney, Agent, or Firm*—Arnold S. Milowsky, Esq.; Cozen O'Connor

(57) ABSTRACT

This invention provides 3β-hydroxy-5,7,9-estratriene-17-one and a pharmaceutically acceptable salt of its 3-sulfate ester, which is useful as an estrogen.

15 Claims, No Drawings

B-RING ESTRATRIENES

BACKGROUND OF THE INVENTION

This application is a divisional of U.S. application Ser. No. 09/063,524 filed Apr. 21, 1998, now U.S. Pat. No. 6,525,039 which claims the benefit of U.S. Provisional Application No. 60/045,422, filed May 2, 1997.

The use of naturally occurring estrogenic compositions of substantial purity and low toxicity such as PREMARIN (conjugated equine estrogens) has become a preferred medical treatment for alleviating the symptoms of menopausal syndrome, osteoporosis/osteopenia in estrogen deficient women and in other hormone related disorders. The estrogenic components of the naturally occurring estrogenic compositions have been generally identified as sulfate esters of estrone, equilin, equilenin, 17-β-estradiol, dihydroequilenin and 17-β-dihydroequilenin-(U.S. Pat. No. 2,834,712). The estrogenic compositions are usually buffered or stabilized with alkali metal salts of organic or inorganic acids at a substantially neutral pH of about 6.5 to 7.5. Urea has also been used as a stabilizer (U.S. Pat. No. 3,608,077). The incorporation of antioxidants to stabilize synthetic conjugated estrogens and the failure of pH control with tris (hydroxymethyl)aminomethane (TRIS) to prevent hydrolysis is discussed in U.S. Pat. No. 4,154,820.

One of the compounds described herein, 3β-hydroxy-5,7,9-estratriene-17-one 3-sulfate ester sodium salt is a minor component of PREMARIN (conjugated equine estrogens). The preparation of 3β-hydroxy-5,7,9-estratriene-17-one is been disclosed by D. Banerjee in Ind. Chim. Belge. Suppl. 2: 435 (1959); however, no utility is provided for this compound.

DESCRIPTION OF THE INVENTION

In accordance with this invention, there is provided 3β-hydroxy-5,7,9-estratriene-17-one or a pharmaceutically acceptable salt of its 3-sulfate ester. The structure of 3β-hydroxy-5,7,9-estratriene-17-one is shown below as compound I:

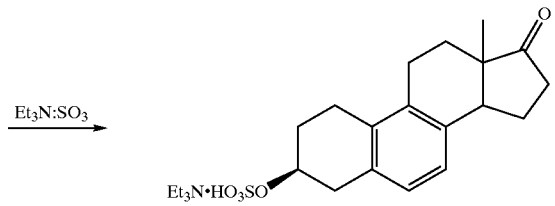

Pharmaceutically acceptable salts of 3β-hydroxy-5,7,9-estratriene-17-one 3-sulfate ester include, but are not limited to, the alkali metal salts, alkaline earth metal salts, ammonium salts, alkylammonium salts containing 1–6 carbon atoms or dialkylammonium salts containing 1–6 carbon atoms in each alkyl group, and trialkylammonium salts containing 1–6 carbon atoms in each alkyl group.

As 3β-hydroxy-5,7,9-estratriene-17-one 3-sulfate ester sodium salt is a minor component of PREMARIN (conjugated equine estrogens), this invention also provides 3β-hydroxy-5,7,9-estratriene-17-one 3-sulfate sodium salt in greater than one percent purity. This invention further provides a compound consisting essentially of a pharmaceutically acceptable salt of 3β-hydroxy-5,7,9-estratriene-17-one 3-sulfate ester; a compound consisting essentially of 3β-hydroxy-5,7,9-estratriene-17-one 3-sulfate ester sodium salt; and a compound consisting essentially of 3β-hydroxy-5,7,9-estratriene-17-one or a pharmaceutically acceptable salt of its 3-sulfate ester.

As used in accordance with this invention, treating covers treatment of an existing condition, ameliorating the condition, or providing palliation of the condition and inhibiting includes inhibiting or preventing the progress or development of the condition.

The compounds of this invention can be prepared from readily available starting materials. For example, the preparation of 3β-hydroxy-5,7,9-estratriene-17-one 3-sulfate ester sodium salt can be prepared from 3β-hydroxy-5,7,9-estratriene-17-one according to Scheme I. 3β-Hydroxy-5,7,9-estratriene-17-one can be prepared according to D. Banerjee in Ind. Chim. Belge. Suppl. 2: 435 (1959).

Scheme I

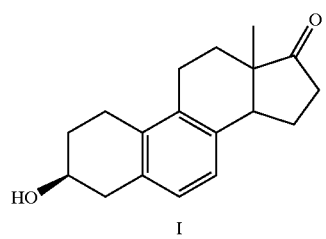

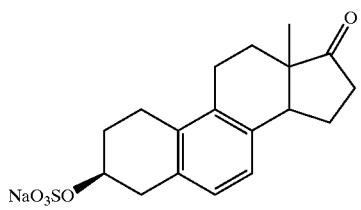

The compounds of this invention are estrogenic, as shown in the in vitro and in vivo standard pharmacological test procedures described below in which 3β-hydroxy-5,7,9-estratriene-17-one was evaluated as a representative compound of this invention.

Estrogen Receptor Binding

An initial evaluation examined the competitive binding properties of 3β-hydroxy-5,7,9-estratriene-17-one to the human estrogen receptor (hER-α) prepared as a soluble cell extract (cytosol). In this standard pharmacological test procedure, 3β-hydroxy-5,7,9-estratriene-17-one demonstrated no specific binding activity. However, when estrogen receptor binding was analyzed using a whole cell test procedure, specific binding was clearly demonstrated. This test procedure indicated an $IC_{50}$ of $7.9 \times 10^{-9}$ M for 3β-hydroxy-5,7,9-estratriene-17-one. This would be compared with a $K_i$ for estrone, equilin and equilinen of 51, 67 and 375 nM, respectively.

In Vitro Cotransfection Test Procedure

In this standard pharmacological test procedure, hER-α over-expressed in Chinese hamster ovary (CHO) cells infected with adeno-2x-ERE-tk-luciferase, an estrogen responsive reporter gene construct, cells were exposed to varying concentrations ($10^{-12}$–$10^{-5}$M) of 3β-hydroxy-5,7,9-estratriene-17-one for 24 hours. Cells were also exposed to 17β-estradiol at $10^{-9}$ M. Following the 24-hour treatment, cells were lysed and cell extracts assayed for luciferase activity. The results provided that 3β-hydroxy-5,7,9-estratriene-17-one had an $EC_{50}$ of approximately 50 nM. Using a similar test procedure, previous data indicate a 5.6 nM $EC_{50}$ for estrone.

In Vivo Uterotropic Activity

Immature rats were treated with 100 μg 3β-hydroxy-5,7,9-estratriene-17-one for three days (S.C.) as well as additional groups (n=6) of rats treated with 0.5 μg ethinyl estradiol and vehicle as positive and negative controls, respectively. Rats treated with 3β-hydroxy-5,7,9-estratriene-17-one had a uterine weight of 54.63±5.2 mg, whereas control rats had uterine weight of 29.78±1.84 mg demonstrating that 3β-hydroxy-5,7,9-estratriene-17-one was estrogenic. Rats treated with ethinyl estradiol (0.5 μg) had a uterine weight of 92.68±7.6 mg.

The results of these standard pharmacological test procedures demonstrate that the compounds of this invention are estrogenic.

A representative compound of this invention (3β-hydroxy-5,7,9-estratriene- 17-one) was evaluated in a standard pharmacological test procedure which measured the cardioprotective effects of the compound tested.

Briefly, Female rats, weighing 180–200 g, were pretreated with DES (0.25 mg/kg, i.p.) 18 hr prior to the study. Uterine horns and aortae were removed from pentobarbital-overdosed animals, cleaned of adherences and cut into 1 cm and 2–3 mm segments, respectively. The preparations were mounted in organ baths containing Jalon solution at 30° C. and Krebs solution at 37° C., respectively, and aerated with 95% $O_2$ and 5% $CO_2$. The contractions were monitored with force-displacement transducers on a Grass polygraph recorder. DMSO produced no effects on the tissues in the present study and thus, was used as a vehicle for dissolving the test compounds.

Both uterine and aortic smooth muscles were contracted with 60 mM KCl. When potassium-induced contraction reached steady-state, cumulative-concentration response curves were determined for test drug or vehicle. Increasing concentrations of the compound to be evaluated were added when the effect of the previous concentration reached steady state (not longer than 20 min). The $EC_{50}$ was defined as the concentration of test compound which produced 50% relaxation.

$EC_{50}$ values of $3.9 \times 10^{-5}$ and $4.0 \times 10^{-5}$ were obtained in uterine muscle and thoracic aorta, respectively, for 3β-hydroxy-5,7,9-estratriene-17-one. These results demonstrate that the compounds of this invention provide cardioprotective protection, particularly in the treatment of ischemic disease and hypertension.

Based on the results obtained in the standard pharmacological test procedures, the compounds of this invention are useful in providing estrogen replacement therapy following ovariectomy or menopause, and in relieving symptoms related to estrogen deficiency, including vasomotor symptoms, such as hot flushes, and other menopausal related conditions, such as vaginal atrophy, vaginitis, and atrophic changes of the lower urinary tract which may cause increased urinary frequency, incontinence, and dysuria. The compounds of this invention are useful in preventing bone loss and in the inhibition or treatment of osteoporosis. The compounds of this invention are cardioprotective and they are useful in the treatment of atherosclerosis, ischemic disease, and hypertension. These cardiovascular protective properties are of great importance when treating postmenopausal patients with estrogens to prevent osteoporosis and in the male when estrogen therapy is indicated. The compounds of this invention are also antioxidants, and are therefore useful in treating or inhibiting free radical induced disease states. Specific situations in which antioxidant therapy is indicated to be warranted are with cancers, central nervous system disorders, Alzheimer's disease, bone disease, aging, inflammatory disorders, peripheral vascular disease, rheumatoid arthritis, autoimmune diseases, respiratory distress, emphysema, prevention of reperfusion injury, viral hepatitis, chronic active hepatitis, tuberculosis, psoriasis, systemic lupus erythematosus, adult respiratory distress syndrome, central nervous system trauma and stroke. Additionally, the compounds of this invention are useful in the suppression of lactation, and in the prophylaxis and treatment of mumps orchitis.

The compounds of this invention can be used alone as a sole therapeutic agent or can be used in combination with other agents, such as other estrogens, progestins, or and androgens.

The compounds of this invention can be formulated neat or with a pharmaceutical carrier for administration, the proportion of which is determined by the solubility and chemical nature of the compound, chosen route of administration and standard pharmacological practice. The pharmaceutical carrier may be solid or liquid.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, lethicins, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellant.

Liquid pharmaceutical compositions which are sterile solutions or suspensions can be utilized by, for example, intramuscular, intraperitoneal or subcutaneous injection. Sterile solutions can also be administered intravenously. The compounds of this invention can also be administered orally either in liquid or solid composition form.

The compounds of this invention may be administered rectally or vaginally in the form of a conventional suppository. For administration by intranasal or intrabronchial inhalation or insufflation, the compounds of this invention may be formulated into an aqueous or partially aqueous solution, which can then be utilized in the form of an aerosol. The compounds of this invention may also be administered transdermally through the use of a transdermal patch containing the active compound and a carrier that is inert to the active compound, is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semipermiable membrane covering a reservoir containing the active ingredient with or without a carrier, or a matrix containing the active ingredient. Other occlusive devices are known in the literature.

The dosage requirements vary with the particular compositions employed, the route of administration, the severity of the symptoms presented and the particular subject being treated. Based on the results obtained in the standard pharmacological test procedures, projected daily dosages of active compound would be 0.02 µg/kg–750 µg/kg. Treatment will generally be initiated with small dosages less than the optimum dose of the compound. Thereafter the dosage is increased until the optimum effect under the circumstances is reached; precise dosages for oral, parenteral, nasal, or intrabronchial administration will be determined by the administering physician based on experience with the individual subject treated. Preferably, the pharmaceutical composition is in unit dosage form, e.g. as tablets or capsules. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form.

The following provides the preparation of 3β-hydroxy-5,7,9-estratriene-17-one 3-sulfate ester sodium salt as a representative compound of this invention.

EXAMPLE 1

3β-Hydroxy-5,7,9-estratriene-17-one 3-sulfate ester sodium salt

Method A:

To a slurry of sodium hydride (60% dispersion in oil, 0.011 g) in THF (6 mL) was added, under nitrogen, at room temperature, 3β-hydroxy-5,7,9-estratriene- 17-one (0.06 g, 0.2 mmol). After stirring for 5 min, triethylamine-sulfurtrioxide complex (0.04 g, 0.21 mmol ) was added and stirring continued for 18 h. Solvent was evaporated off and the residue obtained partitioned between water and diethyl ether (6 mL each). The aqueous solution was separated and lyophilized to provide 0.06 g of the desired product Method B:

To a solution of 3β-hydroxy-5,7,9-estratriene-17-one (0.58 g, 2.1 mmol) in THF (15 mL) at RT, under nitrogen, was added triethylamine-sulfur trioxide complex (0.4 g, 2.3 mmol) and stirred for 48 h. The precipitate formed was filtered off and washed with THF (3×3 mL) and dried to provide 3β-hydroxy-5(10),6, 8-estrtriene-17-one-3-triethylammonium sulfate. (0.71 g, 73.9%).

To a solution of the triethylammonium salt (0.68 g, 1.5 mmol) was added aqueous sodium hydroxide (1 n, 1.6 mL). The solution was stirred for 1 h at RT and repeatedly washed with ether (4×10 mL). The aqueous portion was separated and lyophilized to provide 0.56 g of the desired product.

IR (KBr) 3450, 2930, 1734, 1634, 1238, 1189, 1117, 1069, 980, 978, 810, 620 cm$^{-1}$ $^1$H NMR (DMSO-d$_6$) 6.88 (s, 2H, aromatic), 4.74 (m, 1H, 3-H), 0.64 (s, 3H, 18-Me) $^{13}$C NMR (DMSO-d$_6$) 219.14, 134.80, 133.74, 133.43, 132.25, 126.77, 122.48, 70.45, 46.28, 45.77, 36.02, 35.85, 28.72, 28.39, 23.57, 23.45, 21.28, 12.89

What is claimed is:

1. A method of providing estrogen replacement therapy or treating estrogen deficiency in a mammal in need thereof, which comprises administering an estrogenic amount of a composition comprising greater than 1% by weight 3β-hydroxy-5,7,9-estratriene-17one or a pharmaceutically acceptable salt of its 3-sulfate ester to said mammal.

2. A method of treating vasomotor symptoms related to estrogen deficiency in a mammal in need thereof, which comprises administering an effective amount of a composition comprising greater than 1% by weight 3β-hydroxy-5,7,9-estratriene-17one or a pharmaceutically acceptable salt of its 3-sulfate ester to said mammal.

3. The method of claim 2, wherein the vasomotor symptom is hot flushes.

4. A method of treating or inhibiting osteoporosis in a mammal in need thereof which comprises administering an anti-osteoporosis effective amount of a composition comprising greater than 1% by weight 3β-hydroxy-5,7,9-estratriene-17one or a pharmaceutically acceptable salt of its 3-sulfate ester to said mammal.

5. A method of treating or inhibiting atherosclerosis in a mammal in need thereof which comprises administering an anti-atherosclerosis effective amount of a composition comprising greater than 1% by weight 3β-hydroxy-5,7,9-estratriene-17one or a pharmaceutically acceptable salt of its 3-sulfate ester to said mammal.

6. A method of providing estrogen replacement therapy or treating estrogen deficiency in a mammal in need thereof, which comprises administering an estrogenic amount of 3β-hydroxy-5,7,9-estratriene-17one or a pharmaceutically acceptable salt of its 3-sulfate ester to said mammal, wherein said salt is an alkaline earth metal salt, ammonium salt, alkylammonium salt containing 1–6 carbon atoms, dialkylammonium salt containing 1–6 carbon atoms in each alkyl group or trialkylammonium salt containing 1–6 carbon atoms in each alkyl group.

7. A method of treating vasomotor symptoms related to estrogen deficiency in a mammal in need thereof, which comprises administering an effective amount of 3β-hydroxy-5,7,9-estratriene-17one or a pharmaceutically acceptable salt of its 3-sulfate ester to said mammal, wherein said salt is an alkaline earth metal salt, ammonium salt, alkylammonium salt containing 1–6 carbon atoms, dialkylammonium salt containing 1–6 carbon atoms in each alkyl group or trialkylammonium salt containing 1–6 carbon atoms in each alkyl group.

8. The method of claim 7, wherein the vasomotor symptom is hot flushes.

9. A method of treating or inhibiting osteoporosis in a mammal in need thereof which comprises administering an anti-osteoporosis effective amount of 3β-hydroxy-5,7,9-estratriene-17one or a pharmaceutically acceptable salt of its 3-sulfate ester to said mammal, wherein said salt is an alkaline earth metal salt, ammonium salt, alkylammonium salt containing 1–6 carbon atoms, dialkylammonium salt containing 1–6 carbon atoms in each alkyl group or trialkylammonium salt containing 1–6 carbon atoms in each alkyl group.

10. A method of treating or inhibiting atherosclerosis in a mammal in need thereof which comprises administering an anti-atherosclerosis effective amount of 3β-hydroxy-5,7,9-estratriene-17one or a pharmaceutically acceptable salt of its 3-sulfate ester to said mammal, wherein said salt is an alkaline earth metal salt, ammonium salt, alkylammonium salt containing 1–6 carbon atoms, dialkylammonium salt containing 1–6 carbon atoms in each alkyl group or trialkylammonium salt containing 1–6 carbon atoms in each alkyl group.

11. A method of providing estrogen replacement therapy or treating estrogen deficiency in a mammal in need thereof, which comprises administering an estrogenic amount of a compound which is 3β-hydroxy-5,7,9-estratriene-17one or a pharmaceutically acceptable salt of its 3-sulfate ester to said mammal, wherein said compound is administered as the sole therapeutic agent.

12. A method of treating vasomotor symptoms related to estrogen deficiency in a mammal in need thereof, which comprises administering an effective amount of a compound which 3β-hydroxy-5,7,9-estratriene-17one or a pharmaceutically acceptable salt of its 3-sulfate ester to said mammal, wherein said compound is administered as the sole therapeutic agent.

13. The method of claim 12, wherein the vasomotor symptom is hot flushes.

14. A method of treating or inhibiting osteoporosis in a mammal in need thereof which comprises administering an anti-osteoporosis effective amount of a compound which is 3β-hydroxy-5,7,9-estratriene-17one or a pharmaceutically acceptable salt of its 3-sulfate ester to said mammal, wherein said compound is administered as the sole therapeutic agent.

15. A method of treating or inhibiting atherosclerosis in a mammal in need thereof which comprises administering an anti-atherosclerosis effective amount of a compound which 3β-hydroxy-5,7,9-estratriene-17one or a pharmaceutically acceptable salt of its 3-sulfate ester to said mammal, wherein said compound is administered as the sole therapeutic agent.

* * * * *